United States Patent [19]

Coles et al.

[11] Patent Number: 5,762,642

[45] Date of Patent: Jun. 9, 1998

[54] ABSORBENT ARTICLE, PARTICULARLY SANITARY NAPKIN

[75] Inventors: Peter Coles, Kelkheim-Fischbach; Michael Divo, Friedrichsdorf; Wolfgang Dietmar Schmidt, Liederbach/Ts., all of Germany

[73] Assignee: The Procter & Gamble Company, Cincinnati, Ohio

[21] Appl. No.: 933,564

[22] Filed: Sep. 19, 1997

Related U.S. Application Data

[63] Continuation of Ser. No. 553,386, filed as PCT/US94/04328 Apr. 20, 1994, abandoned.

[30] Foreign Application Priority Data

May 24, 1993 [EP] European Pat. Off. ............ 93108367

[51] Int. Cl.$^6$ ............................ A61F 13/15; A61F 13/20
[52] U.S. Cl. ........................ 604/378; 604/367; 604/372; 604/385.1
[58] Field of Search ...................... 604/358, 367–368, 604/370, 372, 385.1

[56] References Cited

U.S. PATENT DOCUMENTS

| | | | |
|---|---|---|---|
| 3,593,717 | 7/1971 | Jones, Sr. | 604/385.1 |
| 3,693,622 | 9/1972 | Jones, Sr. | 604/385.1 |
| 4,592,751 | 6/1986 | Gegelys. | |
| 4,643,726 | 2/1987 | Gegelys. | |
| 5,151,091 | 9/1992 | Glaug et al.. | |
| 5,171,236 | 12/1992 | Dreier et al.. | |
| 5,192,606 | 3/1993 | Proxmire et al.. | |
| 5,234,422 | 8/1993 | Sneller et al.. | |
| 5,304,159 | 4/1994 | Tanji et al.. | |
| 5,308,346 | 5/1994 | Sneller et al.. | |
| 5,312,386 | 5/1994 | Correa et al.. | |
| 5,382,467 | 1/1995 | Widund et al.. | |
| 5,447,507 | 9/1995 | Yamamoto. | |

FOREIGN PATENT DOCUMENTS

| | | |
|---|---|---|
| 0 072 948 A1 | 3/1983 | European Pat. Off.. |
| 0 335 252 A2 | 10/1989 | European Pat. Off.. |
| 0 597 273 A1 | 5/1994 | European Pat. Off.. |
| 0 600 494 A1 | 6/1994 | European Pat. Off.. |
| 0 605 017 A2 | 7/1994 | European Pat. Off.. |
| WO 90/05514 | 5/1990 | WIPO. |
| WO 90/14814 | 12/1990 | WIPO. |
| WO 93/19715 | 10/1993 | WIPO. |

*Primary Examiner*—John G. Weiss
*Assistant Examiner*—Dennis Ruhl
*Attorney, Agent, or Firm*—Matthew P. Fitzpatrick; Jeffrey V. Bamber; Steven W. Miller

[57] ABSTRACT

An absorbent article, particularly a sanitary napkin comprises a liquid pervious topsheet (12), a liquid impervious backsheet (14) and an absorbent core (16, 18) interposed between the topsheet (12) and the backsheet (14). The core comprises a longitudinal center line and two edges. At least one liquid directing barrier structure is applied to the core and/or the topsheet on either side of the longitudinal center line thereof between the center line and the longitudinal edges.

14 Claims, 3 Drawing Sheets

ABSORBENT ARTICLE, PARTICULARLY SANITARY NAPKIN

This is a continuation of application Ser. No. 08/553,386, filed on Nov. 22, 1995, now abandoned, which is a 371 of PCT/US94/04328 filed Apr. 20, 1994.

The invention relates to an absorbent article, particularly a sanitary napkin comprising a liquid pervious topsheet, a liquid impervious backsheet and an absorbent core interposed between the topsheet and the backsheet, the core comprising a longitudinal center line and two lateral edges.

Absorbent articles of this kind are well-known in the art. These articles, e.g. sanitary napkins, incontinence products or the like, usually have an elongated form with a length-to-width ratio of approximately 3:1. Since the distribution of a liquid applied to the central zone of the napkin will be approximately circular, the liquid will reach the lateral edges of the absorbent core comparatively soon while the suction and liquid storing capacity of the longitudinal end portions of the core cannot be used. Thus, particularly in narrow absorbent articles and/or those having a small caliper, a too large lateral migration of liquids can lead to undesired soiling of the sides of the article.

The U.S. Pat. No. 5,009,653 discloses a sanitary napkin having an absorbent core formed of a layer of hydrogel material interposed between two layers of an air-laid tissue sheet. The core is covered by a wet-laid tissue which series to improve wicking of the discharged body liquids over the core so that a more efficient use of the hydrogel material is made. Thus liquid migration in the longitudinal direction of the sanitary napkin is improved, but lateral migration also occurs and thus soiling of the sides of the napkin remains possible.

The EP-A 0 400 694, teaches to coat a marginal portion of a nonwoven liquid pervious topsheet of an absorbent article by hot melt adhesive to deposit a liquid impermeable film thereon. In connection with babies diapers, it is known from the U.S. Pat. No. 4 795 454 to provide longitudinal barrier cuffs surrounding the leg of a baby and seal lines connecting the barrier cuffs to the backsheet or the topsheet to avoid a lateral escape of body liquids between the backsheets and the barrier cuffs. By laterally sealing an absorbent article, it will be possible to prevent leakage at the longitudinal edges of an absorbent article to some extent, depending on the liquid storing capacity of the edge portions of the absorbent core. However, the possibility to increase the storing capacity of the edge portions by increasing the concentration of superabsorbent gel is limited because of the so-called "gel blocking effect". Moreover, the longitudinal liquid distribution is not substantially improved by this kind of edge barriers.

The GB-A 2 255 720 discloses glue lines extending in the longitudinal direction of the diaper, but these glue patterns only provide an interlayer adhesive connecting the layers of a diaper.

It is an object of the invention to provide an absorbent article of relatively small caliper having a good longitudinal liquid distribution capacity and preventing side soiling at the edges of the article.

It is a further object of the invention to provide an absorbent article in which liquids are first distributed downwards and are subsequently distributed outwardly.

To comply with these objects, an absorbent article according to the invention is characterized by at least one liquid directing barrier structure applied to the core and/or the topsheet on either side of the longitudinal center line between the center line and the longitudinal edges, respectively.

By providing longitudinally directed barrier structures on the core, the lateral migration of the liquid loaded in center portion of the article is substantially reduced or even prevented while the longitudinal migration is improved. Liquids reaching the barrier structures will be deflected and channelled in the longitudinal direction upon filling of the central area of the absorbent structure that is located between the barrier structures.

Thus by applying the barrier structures, the liquid migration can be positively controlled. Blood or other body liquids can be prevented from reaching the sides. Thus the side soiling is reduced or even prevented.

According to a preferred embodiment of the invention, the barrier structures are formed by a liquid-impermeable or a hydrophobic substance penetrating the core from the side of the topsheet at least in part. The barrier structure can extend from the topsheet side substantially to the backsheet, in particular for relatively thin cores that have a caliper of for instance smaller than 3 mm. In case of a core being formed by a folded tissue, having a main portion and two lateral flaps folded onto the back side of the main portion, the hydrophobic substance fully penetrates the main portion. A superabsorbent hydrogel may be interposed between the main portion and the flaps of the tissue.

The barrier structure may have the shape of a single line which may be straight or curved while remaining in the area between the longitudinal center line and the longitudinal edges. The structure may be a spiral line or may consist of dots or dashes, preferably overlapping dashes with respect to the lateral direction, or may have any other suitable pattern.

By applying the liquid-impermeable or hydrophobic substance only to the top portion or the top layer of a multilayer tissue, the liquid is only able to either distribute along the length of the laminate within the barrier structures, which is desired, or travel to the very bottom of the laminate, which is also desired since the absorbent capacity of the absorbent core is fully utilized. Liquid can only pass the barrier structures to reach the longitudinal edges of the absorbent core by migrating down through the absorbent core to the bottom thereof covered by the backsheet and up again through every absorbent layer of the core to the top facing the topsheet.

Preferably, the barrier structures extend over about 10 to 100%, more preferably about 70% of the length of the core.

The barrier structures may be in parallel with each other over the full length. In any case they will be interposed between the longitudinal central line of the article and the longitudinal edges and will be spaced from the longitudinal edges, unlike the conventional longitudinal edge barriers. Thus even if a part of the liquid will pass the barriers as described before, the remaining width of the core between the longitudinal edges and the barriers will be able to store the comparatively small amount of liquid which could escape.

The effect of the invention may be further improved by two or more parallel barrier structures on either side of the longitudinal center line. Pairs of barrier structures may be provided at different heights along the thickness of the core, the distance between the barrier structures in a single pair being larger for the pair located closer to the backsheet.

Barrier structures may be also applied to the topsheet, either in combination with barrier structures in the core or without further barrier structures being present in the core. This is particularly advantageous, if the topsheet consists of a nonwoven material. The barrier structures can also be applied to a so called acquisition sheet. The acquisition sheet forms part of the core and is interposed between the topsheet and a lower absorbent layer of the core.

The term "core" means the absorbent structure, located between the topsheet and the backsheet. The core can comprise one or more tissue layers, a batt of cellulosic and/or synthetic fibers, absorbent foam material or absorbent gelling materials and combinations thereof.

Preferably the barrier structures are spaced away at least by 5 mm from the longitudinal center line on either side, more preferably between 10 and 20 mm, depending on the size of the article. The distance between the barrier structures can comprise between 16% and 100% of the central width of the absorbent article. Especially for relatively narrow absorbent articles such as pantiliners, the barrier structures will be located in close proximity to the longitudinal sides.

The barrier structures may be formed by a wax such as LUNA MELT HS 350, NEU, supplied by H. B. Fuller GmbH, Luneburg, Germany, or a silicon based glue which may be applied by a hot melt nozzle onto the core. In case the core is formed by a tissue laminate, the wax or hot melt may be applied to the tissue, before it is folded, with a vacuum system underneath to ensure the hydrophobic substance fully penetrates the tissue.

The width of each barrier structure may be between 1 and 20 mm, preferably 2 and 10 mm, in particular 3 mm.

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, mensas, and urine). Interiabial devices which reside partially within and partially external of the wearer's vestibule are also within the scope or this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

The sanitary napkin has two surfaces, a body-contacting surface or "body surface" and a garment surface.

The body surface is intended to be worn adjacent to the body of the wearer while the garment surface is on the opposite side and is intended to be placed adjacent to the wearer's undergarments when the sanitary napkin is worn. The sanitary napkin has two centerlines, a longitudinal centerline and a transverse centerline. The term "longitudinal", as used herein, refers to a line, axis or direction in the plane of the sanitary napkin that is generally aligned with (e.g., approximately parallel to) a vertical plane which bisects a standing wearer into left and right body halves when the sanitary napkin is worn. The terms "transverse" or "lateral" as used herein, are interchangeable, and refer to a line, axis or direction which lies within the plane of the sanitary napkin that is generally perpendicular to the longitudinal direction.

While the topsheet, the backsheet, and the absorbent core may be assembled in a variety of well known configurations (including so called "tube" products or side flap products), preferred sanitary napkin configurations are described generally in U.S. Pat. No. 4, 950,264 "Thin, Flexible Sanitary Napkin" issued to Osborn on Aug. 21, 1990 ; U.S. Pat. No. 4,425,130, "Compound Sanitary Napkin" issued to DesMarais on Jan. 10, 1984 ; U.S. Pat. No. 4,321,924, "Bordered Disposable Absorbent Article" issued to Ahr on Mar. 30, 1982 ; U.S. Pat. No. 4,589,876 . "Shaped Sanitary Napkin With Flaps" issued to Van Tilburg on Aug. 18, 1987 . Each of these patents are hereby incorporated herein by reference.

The absorbent core may be any absorbent means which is capable of absorbing retaining liquids (e.g., menses and/or urine). The absorbent core has a body surface, a garment surface, side edges, and pad edges. The absorbent core may be manufactured in a wide variety of sizes and shapes (e.g., rectangular, oval, hourglass, dog bone, asymmetric, etc.) and from a wide variety of liquid-absorbent materials commonly used in sanitary napkin and other absorbent articles such as comminuted wood pulp which is generally referred to as airfelt. Examples of other suitable absorbent materials include creped cellulose wadding; meltblown polymers including coform; chemically stiffened, modified or crosslinked cellulosic fibers; synthetic fibers such as crimped polyester fibers; peat moss; tissue including tissue wraps and tissue laminates; absorbent foams; absorbent sponges; superabsorbent polymers absorbent gelling materials; or any equivalent material or combinations of materials; or mixtures of these. The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinence pads, pantiliner, regular sanitary napkins, or overnight sanitary napkin.

Exemplary absorbent structures for use as the absorbent core of the present invention are described in U.S. Pat. No. 4,950,264 entitled "Thin, Flexible Sanitary Napkin" issued to Osborn on Aug. 21, 1990 ; U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Acquisition Zones" , issued to Alemany et al. on May 30, 1989; and European Patent Application No. 0 198 683, The Procter & Gamble Company, published Oct. 22, 1986 in the name of Duenk, et al. Each of these patents are incorporated herein by reference.

The backsheet and the topsheet are positioned adjacent the garment surface and the body surface, respectively, of the absorbent core and are preferably joined thereto and to each other by attachment means such as those well known in the art. For example, the backsheet and/or the topsheet may be secured to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St.Paul, Min. under the designation HL-1258 or H-2031. The attachment means will preferably comprise an open pattern network of filaments of adhesive as is disclosed un U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet is impervious to liquids (e.g., mensus and/or urine) and is preferably manufactured from a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the sanitary napkin such as pants, pajamas and undergarments. The backsheet may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401and by Ethyl Corporation, Visqueen Division, of Terre Haute, Ind, under the designation XP-39385. The backsheet is preferably embossed and/or matte finished to provide a more clothlike appearance. Further, the backsheet may permit vapors to escape form the absorbent core (i.e., breathable) while still preventing exudates from passing through the backsheet.

The topsheet is compliant, soft feeling, and non-irritating to the wearer's skin. Further the topsheet is liquid pervious permitting liquids (e.g., mensus and or urine) to readily penetrate through its thickness. A suitable topsheet may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester polypropylene, or polyethylene fibers) or from a combination of natural and synthetic fibers. A preferred topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975 ; U.S. Pat. No. 4,324,246 entitled "Disposable Absorbent Article Having A Strain Resistant Topsheet", which issued to Millane, et al. on Apr. 13, 1982 ; U.S. Pat. No. 4,342,314 entitled "Resilient Plastic Web Exhibiting Fiber-Like Properties", which issued to Radel, et al. on Aug. 3, 1982 ; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference. The preferred topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated herein by reference. Alternatively, the body surface of the topsheet can be made hydrophilic by treating it with a surfactant such as is described in the above referenced U.S. Pat. 4,950,254 issued to Osborn, incorporated herein by reference.

In use, the sanitary napkin can be held in place by any support means or attachment means well-known for such purposes. Preferably, the sanitary napkin is placed in the user's undergarment or panty and secured thereto by a fastener such as an adhesive. The adhesive provides a means for securing the sanitary napkin the crotch portion of the panty. Thus, a portion or all of the outer surface 64 of the backsheet 26 is coated with adhesive. Any adhesive or glue used the art for such purposes can be used for the adhesive herein, with pressure-sensitive adhesives being preferred. Suitable adhesives are Century A-305-IV manufactured by the Century Adhesives Corporation of Columbus, Ohio; and Instant Loct 34-2823 manufactured by the National Starch and Chemical Company of Bridgewater, N.J. Suitable adhesive fasteners are also described in U.S. Pat. No. 4,917,697. Before the sanitary napkin is placed is use, the pressure-sensitive adhesive is typically covered with a removable release liner in order to keep the adhesive from drying out or adhering to a surface other than the crotch portion of the panty prior to use. Suitable release liners are also described in the above referenced U.S. Pat. No. 4,917,697. Any commercially available release liners commonly used for such purposes can be utilized herein. Non-limiting examples of suitable release liners are BL30 MG-A Silox E1/0 and BL30 MG-A Silox 4P/0 both of which are manufactured by the Akrosil Corporation of Manasha, Wis. The sanitary napkin of the present invention is used by removing the release liner and thereafter placing the sanitary napkin in a panty so that the adhesive contacts the panty. The adhesive maintains the sanitary napkin in its position within the panty during use.

In a preferred embodiment of the present invention, an acquisition layer(s) may be positioned between the topsheet and the absorbent core. The acquisition layer may serve several functions including improving wicking of exudates over and into the absorbent core. There are several reasons why the improved wicking of exudates is important, including providing a more even distribution of the exudates throughout the absorbent core and allowing the sanitary napkin to be made relatively thin. (The wicking referred to herein may encompass the transportation of liquids in one, two or all directions (i.e. in the x-y plane and/or in the z-direction). The acquisition layer may be comprises of several different materials including nonwoven or woven webs of synthetic fibers including polyester, polypropylene, or polyethylene; natural fibers including cotton or cellulose; blends of such fibers; or any equivalent materials or combinations or materials. Examples of sanitary napkins having an acquisition layer and a topsheet are more fully described in U.S. Pat. No. 4,950,264 issued to Osborn and U.S. patent application Ser. No. 07/810,774, "Absorbent Article Having Fused Layers", filed Dec. 17, 1991 in the names of Cree, et al. Each of these references are incorporated herein by reference. In a preferred embodiment, the acquisition layer may be joined with the topsheet by any of the conventional means for joining webs together, most preferably by fusion bonds as is more fully described in the above-referenced Cree application.

BRIEF DESCRIPTION OF THE DRAWINGS

Some embodiments of an absorbent article according to the present invention will be described in detail with reference to the accompanying drawings, in which:

FIG. 4b is a modification of the cross section of FIG. 4a;

Figure 1:
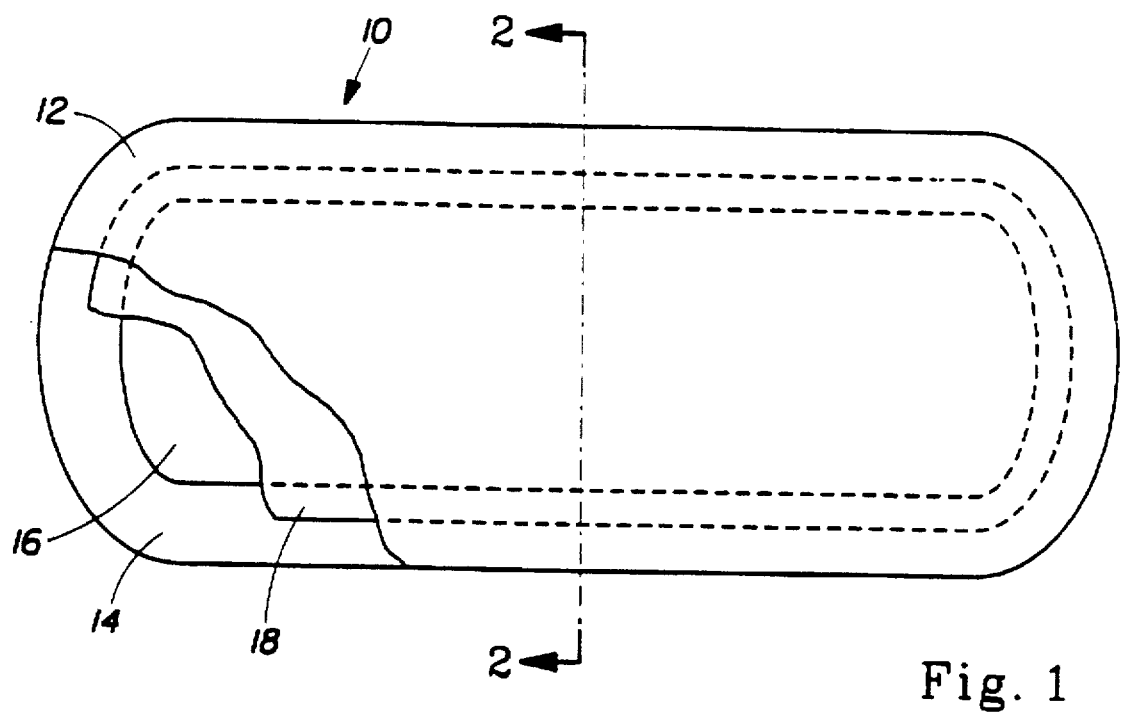
FIG. 1 is a top view on a sanitary napkin forming an embodiment of the invention wherein a part of the overlying layers has been cut away to expose underlying structures.

The embodiments of the absorbent article as illustrated in the drawings refer to a disposable sanitary napkin, i.e. an article which is worn by females adjacent to the pudendal region and which is intended to absorb and contain the various exudates which are discharged from the body (e.g. blood, menses and urine), which is intended to be discarded after a single use. The Invention is however not limited to sanitary napkins only, but also covers other absorbent articles such as pantiliners, which generally have a lower capacity than sanitary napkins or incontinence products. Although the embodiment described in detail in the drawings has a so called "laminate" core wherein the absorbent gelling material is present as a layer between two sheets, the invention is not limited thereto and also applies to cores wherein the absorbent gelling material is mixed with cellulosic and/or fibers, or cores not comprising absorbent gelling materials.

FIG. 1 shows a sanitary napkin 10 comprising a liquid pervious topsheet 12, a liquid impervious backsheet 14 and an absorbent core 16,18 between the topsheet and the backsheet. As shown in FIG. 1, the absorbent core comprises, on the side facing the topsheet 12, a so called acquisition sheet 18 which quickly acquires body liquids and transfers the liquids to the underlying part of the absorbent core. The acquisition sheet may be formed by a wet-laid tissue and serves to improve wicking of the discharged body liquids over the lower parts of the core.

Figure 2:
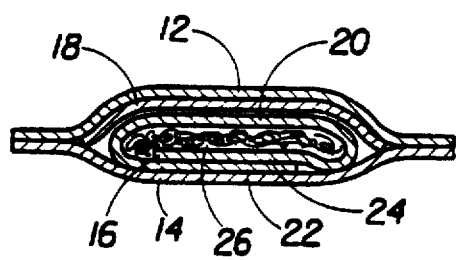
FIG. 2 shows a cross section along the line II—II in FIG. 1.

As shown in FIG. 2, the core 16, 18 comprises a folded tissue comprising a main portion 20 and two lateral flaps 22,24 folded back onto the main portion, thus having a cross section like a vertically compressed letter "e". A superabsorbent hydrogel 26 is interposed between the layers 20,22, 24 of the tissue forming the absorbent core 16.

Figure 3:
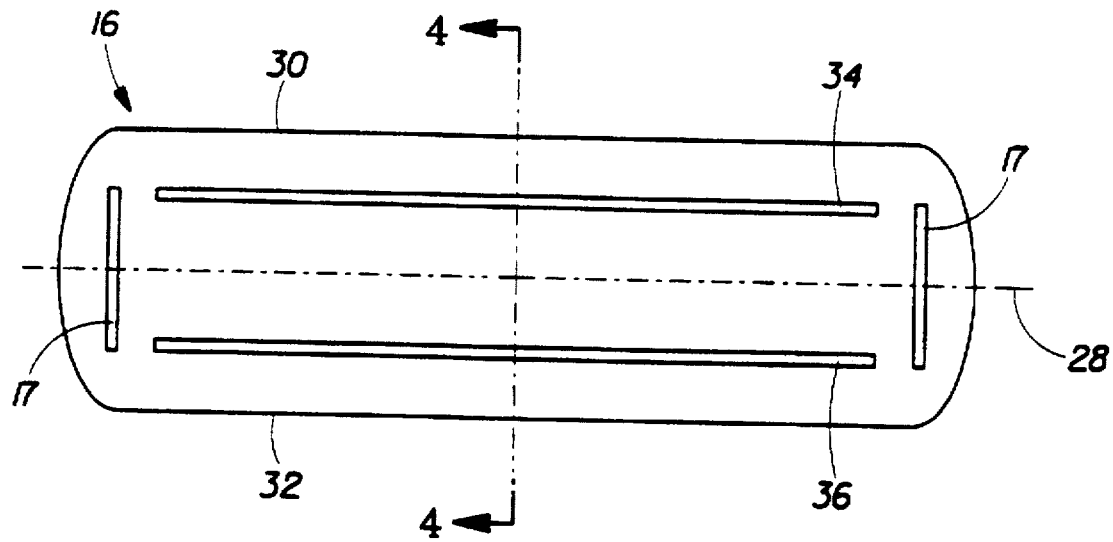
FIG. 3 is a top view on the absorbent core, seen from the side facing the topsheet.

According to FIG. 3, the absorbent core 16,18 of the present embodiment has a straight, elongated shape comprising a longitudinal center line 28 and two longitudinal edges 30 and 32.

As shown more clearly in FIG. 4, the core 16,18 comprises or is formed by a laminate folded tissue comprising the main portion 20 and the two lateral flaps 22,24 folded back onto the main portion 20. The superabsorbent hydrogel 26 is interposed between the main portion 20 and the flaps 22,24 of the tissue.

As may be taken from FIG. 3 and FIG. 4, barrier structures formed by straight parallel barrier lines 34,36 have been applied to the absorbent core on either side of the longitudinal center line 28 of the core. The length of the barrier lines 34,36 may be about 70% of the length of the core.

Figure 4A:
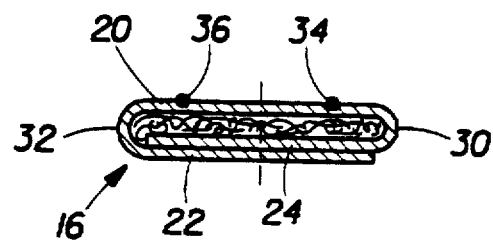
FIG. 4a is a cross section taken along the line I-IV in FIG. 3.

As shown in FIG. 4a, the barrier lines 34,36 only penetrate the laminate structure of the core in part.

According to FIG. 4a, only the main portion 20 of the folded laminate structure of the absorbent core 16,18 is penetrated by the hydrophobic substance.

Figure 4B:
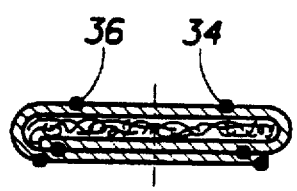

According to FIG. 4b, several pairs of barrier lines are provided in different layers of the core, the lowest barrier lines being spaced apart the furthest.

Any liquid applied to the center portion of the napkin will start to spread circular, and after some time, further lateral migration is prevented or at least substantially reduced and delayed by the barrier lines 34 and 36 which fully keep back any liquid received by the main portion 20. Liquid may only escape below the barrier lines 34,36 but in this case will penetrate down through the hydrogel 26 and the lower layers 22,24 of the laminate and will be substantially stored by these parts of the core, before again migrating to the top side of the core facing the topsheet. At longer loadings, the liquid will be confined within the barrier lines and will be channelled in the longitudinal direction by these lines.

According to FIG. 3, the barrier structures are formed by straight, parallel lines which is considered to be the preferred embodiment, and thus the barrier structures have been designated as barrier lines in the above description. However, modified shapes of the barrier structure are possible.

Figure 5:
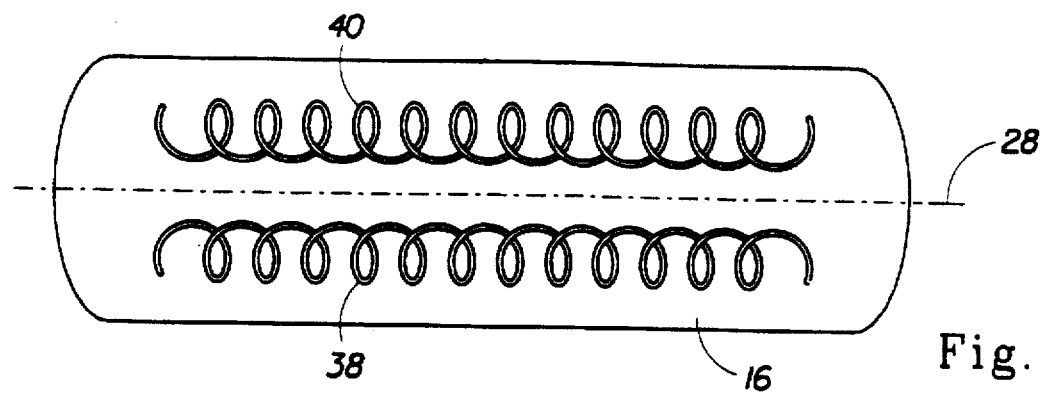
FIGS. 5 to 8 are explanatory top views of modified embodiments of the barrier structures.

FIG. 5 is a top view of an absorbent core 16 to which two spiral barrier lines 38,40 have been applied in a position similar to the position of the barrier lines in FIG. 3.

Figure 6:
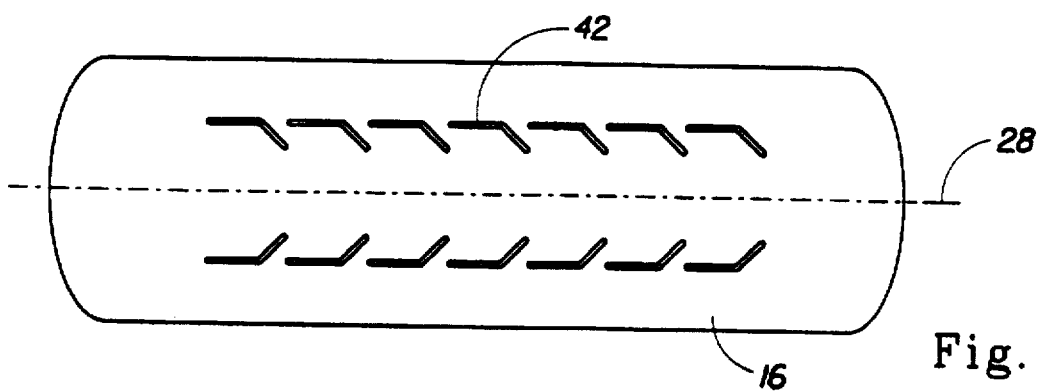

As shown in FIG. 6, it is not absolutely necessary to use closed barrier lines. The barrier structures may be formed by a line of dots or dashes. According to FIG. 6, the dashes 42 may form an obtuse angle at one end directed to the longitudinal center line 28, to provide an overlapping structure of dashes forming a valve system by which migration of liquids into the space between the barrier lines is promoted while migration in the opposite direction is inhibited.

Figure 7:
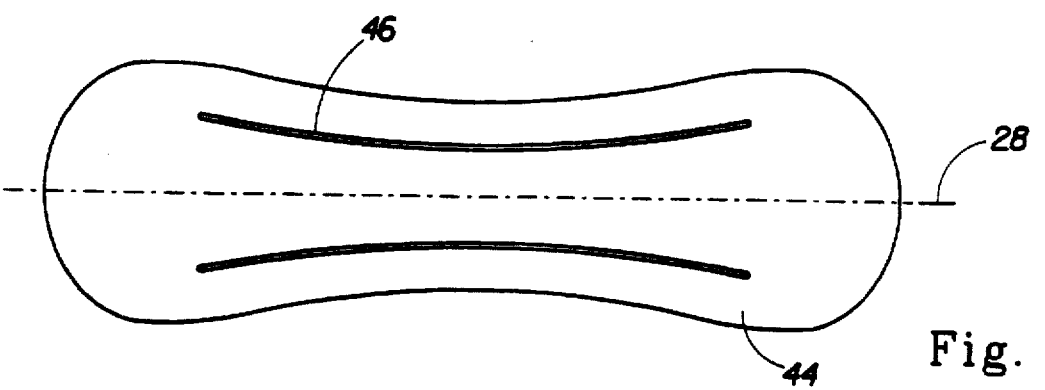
Figure 8:
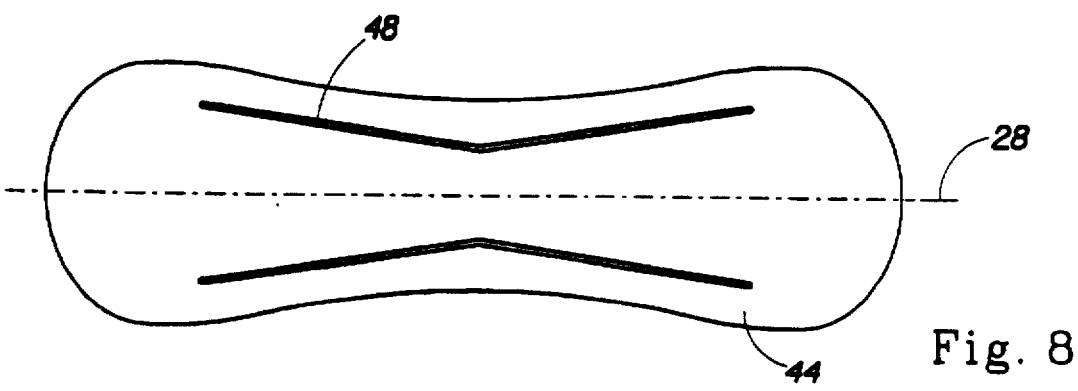

In case of absorbent articles and cores 44 having an hour-glass shape, barrier lines 46,48 may be used which follow the lateral edges (no reference) of the core rather than being straight and parallel with respect to each other, as shown in FIGS. 7 and 8.

The hydrophobic substance may be a wax or a silicon based glue which is applied in a liquid state and cures rapidly.

Tests have been made to compare the absorbent core and the sanitary napkin according to the invention with prior art products. For this purpose, the following samples corresponding to the invention have been used.

Sample #1: Airlaid tissue, comprising pulp held together with adhesive binder, of basis weight 63 g/sqm and caliper 0.64 mm, commercially available for example from Merfin Hygiene Products.

Sample #2: Silicon based spray glue lines on Airlaid tissue (of type outlined in sample #1). 2 parallel lines, 40 mm apart (center to center), 4 mm wide, 65 mm long, totally impregnating the tissue.

Sample #3: Wax lines on Airlaid tissue (of type outlined in sample #1). 2 parallel lines, 40mm apart (center to center), 3 mm wide, 140 mm long, totally impregnating the tissue.

Sample #4: Airlaid tissue laminate encapsulating Absorbent Gelling Material (AGM) according to prior art products. The Airlaid tissue, 138 mm wide, is sprayed with hotmelt adhesive (for example of type Findley L990) with a width of 120 mm, and AGM is applied (for example of type Shokubai L-74) in a concentration of 59.2 g/sqm (5.5 g/sqft). The tissue is then mechanically folded to form an "e" shape AGM laminate of width 64 mm.

Sample #5: Silicon based spray glue lines on AGM laminate (of type outlined in sample #4), impregnating the top laminate tissue layer. Two parallel lines, 20 mm apart (center to center), 4 mm wide, 85 mm long.

Sample #6: AGM laminate (of type outlined in sample #1) with a nonwoven acquisition sheet placed on top. This nonwoven acquisition sheet is made of polyester and viscose, and combined together by hydroentangling. The resulting nonwoven sheet has a symmetric open hole structure and is of basis weight 50 g/sqm), commercially available from JW Suominen OY, for example.

Sample #7: Silicon based spray glue lines on AGM laminate (of type outlined in sample #5) with a nonwoven acquisition sheet (of type outlined in sample #6). 2 parallel lines of silicon based spray glue, 20 mm apart (center to center), 4 mm wide, 85 mm long, also totally impregnating the nonwoven acquisition sheet, in alignment with those on the AGM laminate.

A drip test has been carried out to demonstrate the distribution differences in the samples. In this test, fluid was applied drop-wise at a rate of 1 l/min from a burette, disposed at a height of 5 mm above the sample surface which was placed flat. The samples were suspended over a petry dish to avoid distribution on the ground.

Two fluids were used:

1) Paper Industrial Fluid, a high viscosity solution comprising Carboxmethyl Cellulose (CM), Salts (NaCl, NaHCO$_3$) and water (12.2 Cps at 22° C.).

2) Sheep blood/mucine mixture (1:1).

The results of the test are indicated in the examples given below.

The terms "MD" (Machine Direction) and "CD" (Cross Direction) refer to the longitudinal and lateral directions, respectively, in relation to the pad.

EXAMPLE 1

Single layer absorbent sheet

| Loading (in ml) | Solution | Sample | Distribution (MD × CD) in mm |
|---|---|---|---|
| 0.5 | PIF | #2 | 64 × 16 |
| 0.5 | PIF | #1 (Current tissue) | 45 × 50 |
| 1.0 | Blood/Mucine | #2 | 64 × 14 |
| 1.0 | Blood/Mucine | #1 (Current tissue) | 55 × 56 |
| 2.0 | PIF | #3 | 110 × 38 |
| 2.0 | PIF | #1 (Current tissue) | 45 × 50 |

The tests clearly show that liquids are directed by the liquid barrier lines to spread longitudinally rather than to have a nearly circular distribution. This applies no matter whether the lines are wax (physical barriers) or silicon based glue (chemical barriers).

EXAMPLE 2

AGM Laminate

| Loading (in ml) | Solution | Sample | Distribution (MD × CD) in mm | |
|---|---|---|---|---|
| | | | Top Lam. | Bott. Lam. |
| 2.0 | Blood/Mucine | #5 | 71 × 12 | 71 × 46 |
| 2.0 | Blood/Mucine | #4 | 62 × 60 | 58 × 60 |

On the laminate the benefit of the liquid barrier lines is equally obvious. The results show that the fluid is restricted on the top of the laminate whereas on the conventional laminate, the fluid has almost reached the sides. Moreover, on the core according to the invention, it can be clearly seen that the migration of the liquid is "down and out", i.e. to the bottom (backsheet) and then out to the side edges of the core. Although the results seem to be spectacular when a gap of 20 mm between the barrier lines exists, in reality the lines should be about 40 mm spaced to ensure that almost every liquid load falls between the lines.

EXAMPLE 3

Finished Product (Sanitary napkin comprising absorbent core acc. to the invention)

| Loading (in ml) | Solution | Sample | Distribution (MD × CD) in mm | |
|---|---|---|---|---|
| | | | Top Lam. | Bott. Lam. |
| 6.0 | Blood/Mucine | #7 | 77 × 14 | 160 × 45 |
| 6.0 | Blood/Mucine | #6 | 64 × 70 | 85 × 40 |

The results show the effect of the invention in the finished product. The risk of side soiling is clearly reduced because of the "down and out" migration of the liquid which ensures that at least the by far greatest part of the liquid is captured and stored by the core material before reaching the lateral edges of the core.

What is claimed is:

1. A sanitary napkin comprising a liquid pervious topsheet, a liquid impervious backsheet, and an absorbent core interposed between said topsheet and said backsheet, said absorbent core having a topsheet facing side, a longitudinal center line and two spaced apart side edges, said sanitary napkin comprising at least one liquid directing barrier structure applied to said absorbent core on either side of said longitudinal center line thereof between said center line and said side edges, wherein said liquid directing barrier structure penetrates said topsheet facing side of said absorbent core and only a portion of the remainder of said absorbent core.

2. The sanitary napkin as claimed in claim 1, wherein said barrier structure further penetrates said topsheet.

3. The sanitary napkin as claimed in claim 1, wherein said absorbent core comprises a folded tissue having a main portion and two lateral flaps folded back onto said main portion.

4. The sanitary napkin according to claim 1, wherein said at least one barrier structure is continuous on either side of said longitudinal center line.

5. The sanitary napkin according to claim 1, wherein said at least one barrier structure is discontinuous on either side of longitudinal center line.

6. The sanitary napkin according to claim 1, wherein said at least one barrier structure is in the shape of spirals.

7. The sanitary napkin according to claim 1, wherein said at least one barrier structure extends along about 70% of the length of said absorbent core.

8. The sanitary napkin according to claim 1, wherein said at least one barrier structure comprises a pair of barrier structures that are parallel to each other.

9. The sanitary napkin according to claim 1, wherein said at least one barrier structure is located at least 5 mm perpendicularly from said longitudinal center line.

10. The sanitary napkin according to claim 1, wherein said at least one barrier structure is formed by a wax.

11. The sanitary napkin according to claim 1, wherein said at least one barrier structure is formed by a hydrophobic substance.

12. The sanitary napkin according to claim 1, wherein said at least one barrier structure has a width, said width being at least 2 mm.

13. The sanitary napkin according to claim 1, further comprising a liquid permeable acquisition sheet disposed between the topsheet facing surface of said absorbent core and said topsheet, wherein said at least one barrier structure penetrates said acquisition sheet, thereby attaching said acquisition sheet to the topsheet facing surface of said absorbent core.

14. The sanitary napkin according to claim 1, having longitudinal end portions, wherein said sanitary napkin further comprises transverse liquid directing barriers oriented in a direction perpendicular to said longitudinal center line and located within said longitudinal end portions of said sanitary napkin.

* * * * *